US006224891B1

(12) United States Patent
Rafter et al.

(10) Patent No.: US 6,224,891 B1
(45) Date of Patent: May 1, 2001

(54) COMPOUNDS AND METHODS FOR THE TREATMENT OF BACTERIAL DYSENTERY USING ANTIBIOTICS AND TOXIN BINDING OLIGOSACCHARIDE COMPOSITIONS

(75) Inventors: David John Rafter, Calgary; Robert Murray Ratcliffe, Cochrane; Bradley G. Thompson, Calgary; Glen D. Armstrong, Edmonton, all of (CA)

(73) Assignee: Synsorb Biotech, Inc., Calgary (CA)

( * ) Notice: Subject to any disclaimer, the term of this patent is extended or adjusted under 35 U.S.C. 154(b) by 0 days.

(21) Appl. No.: 09/255,709

(22) Filed: Feb. 23, 1999

Related U.S. Application Data
(60) Provisional application No. 60/075,643, filed on Feb. 23, 1998.

(51) Int. Cl.[7] .................................................. A01N 25/26
(52) U.S. Cl. .......................... 424/421; 424/405; 424/406; 424/407; 424/409; 424/410; 424/417; 514/24; 514/25; 514/42; 514/53; 514/54; 514/61; 514/63
(58) Field of Search .................................. 424/404–407, 424/409–410, 417–421; 514/22–25, 42, 724, 63, 61, 53, 54

(56) References Cited

U.S. PATENT DOCUMENTS

| 4,137,401 | 1/1979 | Lemieux et al. . |
| 4,238,473 | 12/1980 | Lemieux et al. . |
| 4,362,720 | 12/1982 | Lemieux et al. . |
| 5,079,353 | 1/1992 | Ratcliffe et al. . |
| 5,549,895 | 8/1996 | Lyon et al. . |
| 5,552,294 | 9/1996 | Thorne et al. . |

FOREIGN PATENT DOCUMENTS

| WO93/08209 | 4/1993 | (WO) . |
| wo 97/39103 | 10/1997 | (WO) . |
| WO97/49431 | 12/1997 | (WO) . |
| WO98/21220 | 5/1998 | (WO) . |
| WO98/21221 | 5/1998 | (WO) . |
| WO98/21222 | 5/1998 | (WO) . |
| WO98/30572 | 7/1998 | (WO) . |

OTHER PUBLICATIONS

Aleksiev, R., et al., "Influence of Mitomycin C on the Virulence of *Escherichia Coli* O157:H7 Enterohemorrhagic Strain 933 and Its Rec A Negative Mutant Strain in Peroral Infections of White Mice," *Probl. Infect. Parasit. Dis.* 24:32–36 (1997). XP–002105358.

Armstrong, G.D., et al., "A Phase I Study of Chemically Synthesized Verotoxin (Shiga–Like Toxin) PK–Trisaccharide Receptors Attached to Chromosorb for Preventing Hemolytic–Uremic Syndrome," *Journal of Infectious Diseases* 171:1042–1045 (1995).

Ito, T., et al., "Evaluation of Antibiotics Used for Enterohemorrhagic *Escherichia coli* O157 Enteritis—Effect of Varius Antibiotics on Extracellular Release of Verotoxin," *Kansenshogaku Zasshi* 71: 130–135 (1997). XP–00205350.

Karch, H., et al., "Growth of *Escherichia Coli* in the Presence of Trimethoprim—Sulfamethoxazole Facilitates Detection of Shiga–like Toxin Producing Strains by Colony Blot Assay," *Fems Microbiol. Lett.* 35: 141–5 (1986). XP–002105355.

Kobayashi, I. et al., "Therapeutic Effect of Fosfomycin Against Intestinal Infection with *Escherichia Coli* O157: H7 In a Mouse Model. 2. Therapeutic Effects of Fosfomycin at a Large Oral Dose," *Nippon Kagaku Ryoho Gakkai Zasshi* 46: 445–449 (1998). XP–002105353.

Moriguchi, N., et al., "The Drug Sensitivity of Enterohemorrhagic *Escherichia Coli* and Antibiotics Treatment for Hemorrhagic Entercolitis—From an Outbreak of Entercolities in Sakai City," *Jpn. J. Antiobiot.* 50: 591–6 (1997). XP–002105352.

Paton, J.C., et al., "Pathogenesis and diagnosis of Shiga Toxin–producing *Escherichia Coli* Infections," *Clinical Microbiology Reviews* 11: 450–479 (1998). XP–002105349.

Ruggenenti, P., et al., "Treatment of Thrombotic Microangiopahty," *Journal of Nephrology* 8: 255–272 (1995). XP–002105348.

Swerdlow, D.L., et al., "A Waterborne Outbreak in Missouri of *Escherichia Coli* 0157: H7 Associated With Bloody Diarrhea and Death," *Annals of Internal Medicine* 117: 812–819 (1992). XP–002105351.

Takeda, T., et al., "In Vitro Specific Binding of Shiga Toxin 1 and 2 by TAK–751S (Gb3 analog)" *Kansenshogaku Zasshi* 72: 924–34 (1998). XP–002105347.

Ushijima, T., et al., "Environment Factors for Potent Inhibition of Release of Verotoxin of Enterohemorrhagic *Escherichia Coli* in the Anaerobic Growth Condition," *Igaku to Seibutsugaku* 136: 39–44 (1998). XP–002105359.

(List continued on next page.)

*Primary Examiner*—Neil S. Levy
(74) *Attorney, Agent, or Firm*—Burns, Doane, Swecker & Mathis, LLP.

(57) ABSTRACT

This invention relates to the treatment of diarrhea and related conditions caused by pathogenic *E. coli* infection. More specifically, this invention is drawn to the unexpected discovery that by administering a composition which binds and removes the shiga like toxins (SLT) produced by pathogenic *E. coli* whenever an antibiotic is administered, improved treatment is provided. Novel compositions containing both antibiotic and toxin binding composition and methods of treatment which use simultaneous administration toxin binding composition whenever antibiotic is administered are provided. These compositions and methods kill the enteric *E. coli* organisms which produce the conditions and neutralize the SLT produced by the organisms and/or released from the organisms when they are killed. Thus, these compositions and methods are better able to ameliorate the symptoms of the infection and inhibit progression of this infection into hemolytic uremic syndrome (HUS) than conventional treatment.

9 Claims, No Drawings

OTHER PUBLICATIONS

Yee, A.J., et al., "Mitomycin C Induction of A Three Thousand–Fold Increase in Synthesis of a Shiga–like Toxin From Enteropathogenic *Escherichia–Coli* Strain H.1.8," *Abstr. Gen. Meet. Am. Soc. Microbiol.* 92: 131, Abstract No. D214 (1992). XP–002105354.

Yoh, M., et al., "Effect of Antimicrobial Agents, Especially Fosfomycin, on the Production and Release of Vero Toxin by Enterohemorrhagic *Escherichia Coli* O157: H7," *Fems. Immunol. Med. Microbiol.* 19: 57–64 (1997). XP–002105357.

Yoshino, K., et al., "Use of a Verotoxin–absorbent for Preventing Deuteropathy of Enterohemorrhagic *Escherichia Coli* Infection," *Chemical Abstracts* 127: Abstract No. 103714 (1997). XP–002105360.

Yoshino, K., et al., "Use of a Verotoxin–absorbent for Preventing Deuteropathy of Enterohemorrhagic *Escherichia Coli* Infection," *Kagaku Ryoho No Ryoiki* 13 1155–1158 (1997). XP–002105346.

Abbas, S.A., et al., "Tumor–Associated Oligosaccharides I: Synthesis of Sialyl–Lewis$^a$ Antigenic Determinant", *Sialic Acids,* Proc. Japan–German Symp., Berlin, 22–23 (1988).

Amvam–Zollo, P., et al., "*Streptococcus pneumoniae* Type XIV Polysaccharide: Synthesis of a Repeating Branched Tetrasaccharide with Dioxa–Type Spacer–Arms", *Carbohy. Res.,* 150:199–212 (1986).

Armstrong, G.D., et al., *Infect. Immunol.,* 55:1294–1299 (1987).

Armstrong, G.D., et al., *J. Infect. Dis.,* 164:1160–1167 (1991).

Boyd, et al., *Nephron,* 51:207–210 (1989).

Calderwood, et al., *Proc. Natl. Acad. Sci. (USA),* 84:4364–4368 (1987).

Chernyak, A.Y., et al., "A New Type of Carbohydrate–Containing Synthetic Antigen: Synthesis of Carbohydrate–Containing Polyacrylamide Copolymers having the Specificity of 0:3 and 0:4 Factors of Salmonella", *Carbohy. Res.,* 128:269–282 (1984).

Cimolai, et al., *J. Pediatr.,* 117:676 (1990).

Cohen, et al., *J. Biol. Chem.,* 262:17088–17091 (1987).

Cox, D., et al., "A New Synthesis of 4–O–α–D–Galactoopyranosyl–D–Galacto–Pyranose", *Carbohy. Res.,* 62:245–252 (1978).

Dahmén, J., et al., "Synthesis of Space Arm, Lipid, and Ethyl Glycosides of the Trisaccharide Portion [α–D–Gal–(1–4)–β–D–Gal(1–4)–β–D–Glc] of the Blood Group p$^k$ Antigen: Preparation of Neoglycoproteins", *Carbohy. Res.,* 127:15–25 (1984).

Dahmén, J., et al., "2–Bromoethyl Glycosides: Applications in the Synthesis of Spacer–Arm Glycosides", *Carbohy. Res.,* 118:292–301 (1983).

DeGrandis, et al., *J. Biol. Chem.,* 264:12520–12525 (1989).

Ekborg, G., et al., "Synthesis of Three Disaccharides for the Preparation of Immunogens bearing Immunodeterminants Known to Occur on Glycoproteins", *Carbohy. Res.,* 110:55–67 (1982).

Fernandez–Santana, V., et al., "Glycosides of Monallyl Diethylene Glycol. A New type of Spacer group for Synthetic Oligosaccharides", *J. Carbohy. Chem.,* 8(3):531–537 (1989).

Fügedi, P., et al., "Thioglycosides as Glycosylating Agents in Oligosaccharide Synthesis", *Glycoconjugate J.,* 4:97–108 (1987).

Gannon, et al., *J. Gen. Microb.,* 136:1125–1135 (1990).

Garegg, P.J., et al., "A Synthesis of 8–Methoxycarbonyloct–1–yl O–α–D–Galactopyranosyl–(1–3)–O–β–D–Galactopyranosyl–(1–4)–2–Acetamido–2–Deoxy–β–D–Glucopyranoside", *Carbohy. Res.,* 136:207–213 (1985).

Garegg, P.J., et al., "Synthesis of 6– and 6' –deoxy Derivatives of 4–O–α–D–galactopyranosyl–β–D–galactopyranoside for Studies of Inhibition of Pyelonephritogenic Fimbriated *E. coli* Adhesion to Urinary Epithelium–Cell Surfaces", *Carbohy. Res.,* 137:270–275 (1985).

Head, S., et al., *Infect. Immunol.,* 58:1532–1537 (1990).

Head, et al., *FEMS Microb. Lett.,* 51:211–216 (1988).

Ito, et al., *Microb. Pathog.,* 8:47–60 (1990).

Itoh, T., et al., VTEC Abstracts, p. 19 (1997).

Jacewicz, et al., *J. Exp. Med.,* 163:1391–1404 (1986).

Jackson, et al., *Microb. Pathog.,* 2:147–153 (1987).

Jacquinet, J.C., et al., "Synthesis of Blood–group Substances, Part 11. Synthesis of the Trisaccharide O–α–D–Galactopyranosyl–(1–3)–O–β–D–galactopyranosyl–(1–4)–2–acetamido–2–deoxy–D–glucopyranose", *J.C.S. Perkin,* I:326–330 (1981).

Kameyama, A., et al., "Total Synthesis of Sialyl Lewis X", *Carbohy. Res.,* 209:c1–c4 (1991).

Karmali, M.A., et al., *J. Clin. Microb.,* 22:614–619 (1985).

Koike, K., et al., "Total Synthesis of Globotriaosyl–E and Z–Ceramides and Isoglobotriaosyl–E–Ceramide," *Carbohy. Res.,* 163:189–208 (1987).

Lee, R.T., et al., "Synthesis of 3–(2–Aminoethylthio) PropylGlycosides," *Carbohy. Res.,* 37:193–201 (1974).

Lemieux, R.U., et al., "The Properties of a 'Synthetic' Antigen Related to the Blood–Group Lewis A," *J. Am. Chem. Soc.,* 97:4076–83 (1975).

Lindberg, et al., *J. Biol. Chem.,* 262:1779–1785 (1987).

Lingwood, et al., *J. Biol. Chem.,* 262:8834–8839 (1987).

Matsuda, E., et al., VTEC Abstracts, p. 108 (1997).

Okamoto, K., et al., "Glycosidation of Sialic Acid," *Tetrahedron,* 47:5835–5857 (1990).

Oku, et al., *Microb. Pathog.,* 6:113–122 (1989).

Paulsen, H., "Synthese von oligosaccharid–determinanten mit amid–spacer vom typ des T–antigens," *Carbohy. Res.,* 104:195–219 (1982).

Paulsen, "Advances in Selective Chemical Syntheses of Complex Oligosaccharides," *Angew. Chem. Int. Ed. Eng.,* 21:155–173 (1982).

Rana, S.S., et al., "Synthesis of Phenyl 2–Acetamido–2–Deoxy–3–O–α–L–Fucopyranosyl–β–D–Glucopyranoside and Related Compounds," *Carbohy. Res.,* 91:149–157 (1981).

Robson, et al., *J. Pediatr.,* 117:675–676 (1990).

Samuel, et al., *Infect. Immunol.,* 58:611–618 (1990).

Schaubach, R., et al., "Tumor–Associated Antigen Synthesis: Synthesis of the Gal–α–(1–3)–Gal–β–(1–4)–GlcNAc Epitope. A Specific Determinant for Metastatic Progression?", *Liebigs Ann. Chem.,* 607–614 (1991).

Schmidt, "New Methods for the Synthesis of Glycosides and Oligosaccharides—Are There Alternatives to the Koenigs–Knorr Method?", *Angew. Chem. Int. Ed. Eng.,* 25:212–235 (1986).

Schmitt, et al., *Infect. Immun.,* 59:1065–1073 (1991).

Scotland, et al., *Lancet,* ii:885–886 (1991).

Strockbine, et al., *J. Bacteriol.,* 170:1116–1122 (1988).

Waddell, et al., *Biochem. Biophys. Res. Comm.,* 152:674–679 (1988).

Waddell, et al., *Proc. Natl. Acad. Sci. (USA)*, 87:7898–7901 (1990).

Walterspiel, J.N., et al., *Infection,* 20:25–29 (1992).

Weinstein, et al., *J. Bacteriol.,* 170:4223–4230 (1988).

Yamamoto, T., et al., VTEC Abstracts, p. 115 (1997).

COMPOUNDS AND METHODS FOR THE TREATMENT OF BACTERIAL DYSENTERY USING ANTIBIOTICS AND TOXIN BINDING OLIGOSACCHARIDE COMPOSITIONS

CROSS-REFERENCE TO RELATED APPLICATIONS

This application claims priority to U.S. Application Ser. No. 60/075,643 filed Feb. 23, 1998, the disclosure of which is incorporated herein by reference in its entirety.

BACKGROUND OF THE INVENTION

Field of the Invention

This invention relates to the treatment of diarrhea and related conditions caused by pathogenic E. coli infection. More specifically, this invention is drawn to the unexpected discovery that by administering a composition which binds and removes the shiga like toxins (SLT) produced by pathogenic E. coli whenever an antibiotic is administered, improved treatment is provided. Novel compositions containing both antibiotic and toxin binding composition and methods of treatment which use simultaneous administration of toxin binding composition whenever antibiotic is administered are provided. These compositions and methods kill the enteric E. coli organisms which produce the conditions and neutralize the SLT produced by the organisms and/or released from the organisms when they are killed. Thus, these compositions and methods are better able to ameliorate the symptoms of the infection and inhibit progression of this infection into hemolytic uremic syndrome (HUS) than conventional treatment.

References

The following references are cited in the application as numbers in brackets ([]) at the relevant portion of the application.

1. Karmali, M. A., et al., *J. Clin. Microb.,* 22:614–619 (1985).

2. Head, S., et al., *Infect. Immunol.,* 58:1532–1537 (1990).

3. Samuel, et al., *Infect. Immunol.,* 58:611–618 (1990).

4. Altman, D. G., *Practical Statistics for Med. Res.,* 1st ed., New York, Chapman and Hall: 179–228 (1991).

5. Calderwood, et al., *Proc. Natl. Acad. Sci. (USA),* 84:4364–4368 (1987).

6. Jackson, et al., *Microb. Pathog.,* 2:147–153 (1987).

7. Strockbine, et al., *J. Bacteriol.,* 170:1116–1122 (1988).

8. Robson, et al., *J. Pediatr.,* 117:675–676 (1990).

9. Cimolai, et al., *J. Pediatr.,* 117:676 (1990).

10. Armstrong, et al., International Patent Application Publication No. WO 93/08209, for "DIAGNOSIS AND TREATMENT OF BACTERIAL DYSENTERY, published Apr. 29, 1993.

11. Lemieux, R. U., et al., "The Properties of a 'Synthetic' Antigen Related to the Blood-Group Lewis A", *J. Am. Chem. Soc.,* 97:4076–83 (1975).

12. Lemieux, R. U., et al., "Glycoside-Ether-Ester Compounds", U.S. Pat. No. 4,137,401, issued Jan. 30, 1979.

13. Lemieux, R. U., et al., "Artificial Oligosaccharide Antigenic Determinants", U.S. Pat. No. 4,238,473, issued Dec. 9, 1980.

14. Lemieux, R. U., et al., "Synthesis of 2-Amino-2-Deoxyglycoses and 2-Amino-2-Deoxyglycosides from Glycals", U.S. Pat. No. 4,362,720, issued Dec. 7, 1982.

15. Cox, D., et al., "A New Synthesis of 4-0-α-D-Galactopyranosyl-D-Galacto-Pyranose", *Carbohy. Res.,* 62:245–252 (1978).

16. Dahmén, J., et al., "Synthesis of Space Arm, Lipid, and Ethyl Glycosides of the Trisaccharide Portion [α-D-Gal-(1-4)-β-D-Gal(14-4)-β-D-Glc] of the Blood Group p$^k$ Antigen: Preparation of Neoglycoproteins", *Carbohy. Res.,* 127:15–25 (1984).

17. Garegg, P. J., et al., "A Synthesis of 8-Methoxycarbonyloct-1-yl O-α-D-Galactopyranosyl-(1-3)-0-β-D-Galactopyranosyl-(1-4)-2-Acetamido-2-Deoxy-β-D-Glucopyranoside", *Carbohy. Res.,* 136:207–213 (1985).

18. Garegg, P. J., et al., "Synthesis of 6- and 6'-deoxy Derivatives of Methyl 4-0-α-D-galactopyranosyl-β-D-galactopyranoside for Studies of Inhibition of Pyelonephritogenic Fimbriated E. coli Adhesion to Urinary Epithelium-Cell Surfaces", *Carbohy. Res.,* 137:270–275 (1985).

19. Jacquinet, J. C., et al., "Synthesis of Blood-group Substances, Part 11. Synthesis of the Trisaccharide O-α-D-Galactopyranosyl-(1-3)-0-β-D-galactopyranosyl-(1-4)-2-acetamido-2-deoxy-D-glucopyranose", *J.C.S. Perkin,* 1:326–330 (1981).

20. Koike, K., et al., "Total Synthesis of Globotriaosyl-E and Z-Ceramides and Isoglobotriaosyl-E-Ceramide," *Carbohy. Res.,* 163:189–208 (1987).

21. Schaubach, R., et al., "Tumor-Associated Antigen Synthesis: Synthesis of the Gal-α-(1-3)-Gal-β-(1-4)-GlcNAc Epitope. A Specific Determinant for Metastatic Progression?", *Liebigs Ann. Chem.,* 607–614 (1991).

22. Ratcliffe, R. M., et al., "Sialic Acid Glycosides, Antigens, Immunoadsorbents, and Methods for Their Preparation", U.S. Pat. No. 5,079,353, issued Jan. 7, 1992.

23. Okamoto, K., et al., "Glycosidation of Sialic Acid," *Tetrahedron,* 47:5835–5857 (1990).

24. Abbas, S. A., et al., "Tumor-Associated Oligosaccharides I: Synthesis of Sialyl-Lewis$^a$ Antigenic Determinant", *Sialic Acids, Proc. Japan-German Symp.,* Berlin, 22–23 (1988).

25. Paulsen, "Advances in Selective Chemical Syntheses of Complex Oligosaccharides", *Angew. Chem. Int. Ed. Eng.,* 21:155–173 (1982).

26. Schmidt, "New Methods for the Synthesis of Glycosides and Oligosaccharides—Are There Alternatives to the Koenigs-Knorr Method?", *Angew. Chem. Int. Ed. Eng.,* 25:212–235 (1986).

27. Fügedi, P., et al., "Thioglycosides as Glycosylating Agents in Oligosaccharide Synthesis", *Glycoconjugate J.,* 4:97–108 (1987).

28. Kameyama, A., et al., "Total Synthesis of Sialyl Lewis X", *Carbohy. Res.,* 209:c1–c4 (1991).

29. Ekborg, G., et al., "Synthesis of Three Disaccharides for the Preparation of Immunogens bearing Immunodeterminants Known to Occur on Glycoproteins", *Carbohy. Res.,* 110:55–67 (1982).

30. Dahmén, J., et al., "2-Bromoethyl Glycosides: Applications in the Synthesis of Spacer-Arm Glycosides", *Carbohy. Res.,* 118:292–301 (1983).

31. Rana, S. S., et al., "Synthesis of Phenyl 2-Acetamido-2-Deoxy-3-O-α-L-Fucopyranosyl-β-D-Glucopyranoside and Related Compounds", *Carbohy. Res.,* 91:149–157 (1981).

32. Amvam-Zollo, P., et al., "Streptococcus pneumoniae Type XIV Polysaccharide: Synthesis of a Repeating Branched Tetrasaccharide with Dioxa-Type Spacer-Arms", *Carbohy. Res.,* 150:199–212 (1986).

33. Paulsen, H., "Synthese von oligosaccharid-determinanten mit amid-spacer vom typ des T-antigens", *Carbohy. Res.*, 104:195–219 (1982).

34. Chernyak, A. Y., et al., "A New Type of Carbohydrate-Containing Synthetic Antigen: Synthesis of Carbohydrate-Containing Polyacrylamide Copolymers having the Specificity of 0:3 and 0:4 Factors of Salmonella", *Carbohy. Res.*, 128:269–282 (1984).

35. Fernandez-Santana, V., et al., "Glycosides of Monoallyl Diethylene Glycol. A New type of Spacer group for Synthetic Oligosaccharides", *J. Carbohy. Chem.*, 8(3):531–537 (1989).

36. Lee, R. T., et al., "Synthesis of 3-(2-Aminoethylthio) PropylGlycosides", *Carbohy. Res.*, 37:193–201 (1974).

37. Gannon, et al., *J. Gen. Microb.*, 136:1125–1135 (1990).

38. Weinstein, et al., *J. Bacteriol.*, 170:4223–4230 (1988).

39. Ito, et al., *Microb. Pathog.*, 8:47–60 (1990).

40. Head, et al., *FEMS Microb. Lett.*, 51:211–216 (1988).

41. Schmitt, et al., *Infect. Immun.*, 59:1065–1073 (1991).

42. Scotland, et al., *Lancet*, ii:885–886 (1991).

43. Oku, et al., *Microb. Pathog.*, 6:113–122 (1989).

44. Boyd, et al., *Nephron*, 51:207–210 (1989).

45. DeGrandis, et al., *J. Biol. Chem.*, 264:12520–12525 (1989).

46. Waddell, et al., *Biochem. Biophys. Res. Comm.*, 152:674–679 (1988).

47. Lingwood, et al., *J. Biol. Chem.*, 262:8834–8839 (1987).

48. Waddell, et al., *Proc. Natl. Acad. Sci. (USA)*, 87:7898–7901 (1990).

49. Cohen, et al., *J. Biol. Chem.*, 262:17088–17091 (1987).

50. Jacewicz, et al., *J. Exp. Med.*, 163:1391–1404 (1986).

51. Lindberg, et al., *J. Biol. Chem.*, 262:1779–1785 (1987).

52. Armstrong, G. D., et al., *Infect. Immunol.*, 55:1294–1299 (1987).

53. Armstrong, G. D., et al., *J. Infect. Dis.*, 164:1160–1167 (1991).

54. Rafter, D. J., et al., WO 97/49431 (1997).

55. Matsuda, E., et al., VTEC Abstracts, page 108 (1997).

56. Itoh, T., et al., VTEC Abstracts, page 19 (1997).

57. Yamamoto, T., et al., VTEC Abstracts, page 115 (1997).

58. Hinsgaul, O., et al., WO 98/21220 (1997).

59. Hinsgaul, O., et al., WO 98/21221 (1997).

60. Hinsgaul, O., et al., WO 98/21222 (1997).

61. Yeske, et al., PCT based on U.S. Ser. No. 08/781,327 (1998).

62. Walterspiel, J. N., et al., *Infection*, 20:25–29 (1992).

The disclosure of the above publications, patents and patent application are herein incorporated by reference in their entirety to the same extent as if the language of each individual publication, patent and patent application were specifically and individually included herein.

STATE OF THE ART

Diarrhea caused by strains of pathogenic *E. coli* has been found to be associated with the production of a variety of enterotoxins. Some pathogenic *E. coli* produce enterotoxins that are closely related to the shiga toxin associated with Shigella-caused dysentery. The first member of the family of shiga-like toxins (SLT) to be isolated was cytotoxic for African Green Monkey (Vero) cells and was originally called verotoxin. Since its structural similarity to shiga toxin has been established by sequencing of the relevant genes, this toxin is now more commonly called shiga-like toxin I (SLTI) [5,6,7].

Additional members of the SLT family have subsequently been isolated that can be distinguished serologically, on the basis of gene sequence, or on host specificity [37–43]. Various types of SLTII have been described and have been assigned various designations depending on the strain of *E. coli* from which they are isolated and the host affected. Thus variants have been designated SLTII; vtx2ha; SLTIIvh; vtx2hb; SLTIIc; SLTIIvp and so forth.

All of the SLT are multimeric proteins composed of an enzymatic (A) subunit and multiple (B) subunits. The B oligomer is the binding portion of the toxin that allows it to bind to host cell receptors. The B subunits of SLTI, SLTII and SLTIIvh recognize host cell globoseries glycolipid receptors containing at minimum the disaccharide subunit αGal(1-4)βGal at the non-reducing terminus; SLTIIvp has been shown to bind to the receptors containing this subunit but not necessarily to the non-reducing end [2,44–51]. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLT may cause damage that can result in renal failure and hemoglobin in the urine. SLT are the causative agent in the hemolytic-uremic syndrome. SLT may also be partially involved in the pathogenesis of hemorrhagic colitis (bloody diarrhea). The hemolytic uremic syndrome (HUS) is the leading cause of acute renal failure in childhood and affects approximately 7–10% of children in the 5–10 days following infection with *E. coli* O157:H7 and other verotoxin/shiga-like toxin producing *E. coli* (VTEC).

Recent attention regarding such pathogenic *E. coli* has focused on the known correlation between *E. coli* contamination of certain meats and subsequent infection in humans after ingestion of this meat. The problem is particularly acute with regard to hamburger meat where ingestion of undercooked meat has been found to be the causative factor in the infection. This problem is compounded by the fact that the rapid progression of the pathogenic *E. coli* infection into HUS via the expression of the SLT suggests the hypothesis that initial colonization of the intestinal tract is followed by endothelial injury and subsequent kidney involvement via the transmembrane delivery of the SLT toxin into the blood stream of the infected individual.

As a complicating factor, the art has suggested against the use of antibiotics in the treatment of enterohemorrhagic *E. coli* infection [8], although a recent publication suggested that early administration of antibiotics may result in lower levels of verotoxin [55]. At least in part, antibiotics have been have been contraindicated for treating such conditions because of release of toxins into the gut from the organisms killed by the antibiotic exacerbates the diarrhea and other conditions caused by the toxins. Some studies suggest that antibiotic treatment at or below the minimal inhibitory concentration (MIC) of *E. coli* O157:H7 may, in fact, induce production of verotoxins by the organisms [62]. If so, this would likely increase the chance of HUS developing and would further contradict treatment of such infections with antibiotics. The use of antimotility drugs also appears to be counterproductive [9].

One reported method for the treatment of such infections is to orally administer a pharmaceutically acceptable inert affinity support comprising an αGal(1→4)βGal subunit to the infected patient [10]. This support passes into the intestinal tract of the patient whereupon the αGal(1→4)βGal subunit binds the Shiga-like toxin. Subsequently, the toxin bound to this solid support is eliminated from the body as part of the stool. This procedure is one of the first, if only, reported methods for removing such toxins from the body which, in turn, inhibits manifestation of the conditions associated with toxin accumulation. It has also been shown that the clinical incidence of HUS arising from enterohemorrhagic *E. coli* infection is reduced by the time critical administration of a pharmaceutical composition comprising a pharmaceutically acceptable inert affinity support comprising an αGal(1→4)βGal subunit which subunit binds the SLT. Specifically, it has been found that the clinical incidence of HUS arising from enterohemorrhagic *E. coli* infection is reduced when this pharmaceutical composition is administered within 3 days of presentation of the infection [54,55].

Notwithstanding the significant advances made by these reported methods, further advances in the treatment of enterohemorrhagic *E. coli* infections are needed in order to reduce the occurrence of HUS and the high mortality levels associated therewith. In particular, compounds and methods which can both kill enterohemorrhagic *E. coli* organisms and neutralize and remove SLT are needed. A preferred compound would be administered noninvasively, such as orally, in a suitable pharmaceutical formulation.

SUMMARY OF THE INVENTION

This invention is directed to the surprising and unexpected discovery that enterohemorrhagic *E. coli* infection may be advantageously treated by the simultaneous administration of a composition which binds SLT whenever an antibiotic is administered to a subject suffering from or susceptible to pathogenic *E. coli* infection. Specifically, toxin binding compositions comprising a pharmaceutically acceptable inert affinity support comprising an oligosaccharide which binds the SLT are provided. Particularly useful are oligosaccharides comprising the αGal(1→4)βGal subunit. Such simultaneous administration may, preferably, be accomplished by the use of pharmaceutical compositions comprising both an antibiotic and a pharmaceutically acceptable inert affinity support comprising an oligosaccharide which binds the SLT. The invention provides compositions and methods for the prevention and treatment of pathogenic, and, particularly, enterohemorrhagic E. coli infections.

In one aspect, the invention provides a method to prevent or ameliorate one or more conditions mediated by enterohemorrhagic *E. coli* in a patient suffering from or susceptible to said condition, comprising simultaneously administering to the patient an effective amount of at least one antibiotic and an effective amount of at least one SLT binding oligosaccharide sequence covalently attached to a pharmaceutically acceptable inert support (oligosaccharide-support), wherein said oligosaccharide sequence binds SLT, and wherein the SLT bound to oligosaccharide-support is capable of being eliminated from the gastrointestinal tract. Embodiments where the antibiotic is cefixime, tetracycline, ciprofloxacin, co-trimoxazole, mitomycin-C, fosfomycin or kanamycin; the oligosaccharide comprises the αGal(1→4)βGal subunit, especially where the oligosaccharide is selected from the group consisting of αGal(1→4)βGal, αGal(1→4)βGal(1→4)βGlcNAc and αGal(1→4)βGal(1→4)βGlc; and the oligosaccharide is bound to the support using a non-peptidyl linker are particularly useful. In a preferred embodiment, a single pharmaceutical composition containing the antibiotic and the SLT binding oligosaccharide-support is administered. In another preferred embodiment, the administration is performed within about 3 days of presentation of the infection.

In a further aspect, the invention provides a pharmaceutical composition useful in treating or preventing conditions associated with enterohemorrhagic *E. coli*, comprising at least one antibiotic which is effective against said enterohemorrhagic *E. coli* and at least one oligosaccharide sequence covalently attached to a pharmaceutically acceptable inert support (oligosaccharide-support), wherein said oligosaccharide sequence binds SLT, and a pharmaceutically acceptable carrier, wherein the SLT bound to said oligosaccharide-support is capable of being eliminated from the gastrointestinal tract. Embodiments where the antibiotic is cefixime, tetracycline, ciprofloxacin, co-trimoxazole, mitomycin-C, fosfomycin or kanamycin; the oligosaccharide comprises the αGal(1→4)βGal subunit, especially where the oligosaccharide is selected from the group consisting of αGal(1→4)βGal, αGal(1→4)βGal(1→4)βGlcNAc and αGal(1→4)βGal(1→4)βGlc; and the oligosaccharide is bound to the support using a non-peptidyl linker are particularly useful. In a preferred embodiment, the composition is administered within about 3 days of presentation of the infection.

In another aspect, the invention provides a method to prevent or ameliorate one or more conditions mediated by enterohemorrhagic *E. coli* in a patient suffering from or susceptible to said condition, comprising first administering to the patient an effective amount of at least one SLT binding oligosaccharide sequence covalently attached to a pharmaceutically acceptable inert support (oligosaccharide-support), wherein said oligosaccharide sequence binds SLT, followed by simultaneously administering to the patient an effective amount of at least one antibiotic and an effective amount of at least one SLT binding oligosaccharide sequence covalently attached to a pharmaceutically acceptable inert support (oligosaccharide-support), wherein said oligosaccharide sequence binds SLT, and wherein, following each administration, the SLT bound to the oligosaccharide-support is capable of being eliminated from the gastrointestinal tract. Embodiments where the antibiotic is cefixime, tetracycline, ciprofloxacin, co-trimoxazole, mitomycin-C, fosfomycin or kanamycin; the oligosaccharide comprises the αGal(1→4)βGal subunit, especially where the oligosaccharide is selected from the group consisting of αGal(1→4)βGal, αGal(1→4)βGal(1→4)βGlcNAc and αGal(1→4)βGal(1→4)βGlc; and the oligosaccharide is bound to the support using a non-peptidyl linker are particularly useful. In a preferred embodiment, a single pharmaceutical composition containing the antibiotic and the SLT binding oligosaccharide-support is administered following the initial administration of toxin binding composition alone. In another preferred embodiment, the administration is performed within about 3 days of presentation of the infection.

DESCRIPTION OF THE PREFERRED EMBODIMENTS

As noted above, this invention is directed to the simultaneous co-administration of SLT binding oligosaccharide-support compositions which bind SLT whenever antibiotics which are effective against enterohemorrhagic *E. coli* are administered. This co-administration results in a more effective therapeutic regimen for the prevention of HUS and other conditions related to pathogenic *E. coli* infection. With the toxin-binding composition present, toxins released when the antibiotic kills the microorganism are neutralized and removed from the body. Thus, these methods are better able to ameliorate the symptoms of the infection and inhibit progression of this infection into hemolytic uremic syndrome (HUS) than conventional treatment.

A. Definitions

As used herein the following terms have the following meanings:

The term "biocompatible" refers to chemical inertness with respect to animal or human tissues or body fluids. Biocompatible materials are non-sensitizing.

The term "compatible linker arm" refers to a moiety which serves to space the oligosaccharide structure from the biocompatible support and which is bifunctional wherein one functional group is capable of covalently binding to a reciprocal functional group of the support and the other functional group is capable of binding to a reciprocal functional group of the oligosaccharide structure. Compatible linker arms preferred in the present invention are non-peptidyl linker arms. That is to say that the linker arms do not employ a peptide group to link the oligosaccharide structure to the support. The oligosaccharide may be linked via an 8-methoxycarbonyloctyl linker or via another appropriate non-peptidyl linker, such as a urea-like linker arm of the formula $—NH—(CH_2)_m—NHC(O)NH—$, where m is an integer of from about 2 to about 10.

"Hemolytic uremic syndrome" or "HUS" is considered to be present if there is renal injury and either hemolysis or thrombocytopenia. Renal injury requires an elevation in the serum creatinine concentration (>50 $\mu$mol/L for those less than 5 years, or >60 $\mu$mol/L for those 5–6 years) or a difference in the recorded creatinine values during the acute phase of the illness of more than 50% or at least 10 red blood cells per high power field on urine microscopy. Hemolysis is judged to be present if the hemoglobin concentration is $\leqq$105 g/L or if there are red blood cell fragments on the smear or if a red blood cell transfusion was administered before the hemoglobin dropped to $\leqq$105 g/L. Thrombocytopenia is defined as a platelet concentration of less than $150\times10^9$/L.

The term "oligosaccharide" means saccharides comprising 1 to about 20 saccharide moieties. Saccharide derivatives may also be used as saccharide moieties included in the term oligosaccharide [58–60].

The term "organ involvement" refers to clinically defined organ involvement mediated by SLT which correlates to the natural progression of the disease. Organs other than the intestines include, by way of example, the kidney, heart, elements of the central nervous system ("CNS") (i.e., brain, spinal cord, etc.), liver, and the like. Conventional blood chemistry tests can evaluate liver, heart, and kidney involvement whereas clinical symptoms including dementia, convulsions, disorientation, etc. are employed to determine CNS involvement.

The term "shiga-like toxin" or "SLT" or "verotoxin" refers to a group of toxins produced by enterohemorrhagic *E. coli* that resemble the Shigella-produced shiga toxins as is commonly understood in the art. These toxins comprise an enzymatically active A subunit and a multimeric receptor binding B subunit. Such SLT include SLTI and the various grouped toxins designated in the art as SLTII. Rapid tight binding of SLT to oligosaccharide-support compositions may be demonstrated by assays known to the art, such as the verocytotoxicity neutralization assay.

The term "support" refers to an inert material to which the oligosaccharide sequences are bound, usually via a compatible linker arm. Where use is in vivo, the support will be biocompatible.

The term "SYNSORB" refers to synthetic 8-methoxycarbonyloctyl oligosaccharide structures covalently coupled to CHROMOSORB P™ (Manville Corp., Denver, Colo.) [11], which is a derivatized silica particle. Synthetic oligosaccharide sequences covalently attached to a biocompatible support, e.g., CHROMOSORB P™ (SYNSORB) may be used to bind SLT toxins or verotoxins. These compositions are useful to prevent HUS and associated conditions. SYNSORB is particularly preferred for these compositions because it is non-toxic and resistant to mechanical and chemical degradation. SYNSORBs have been found to pass unaffected through the rat gastrointestinal tract. They were found to be eliminated completely and rapidly (99% eliminated in 72 hours) following oral administration. Additionally, the high density of oligosaccharide moieties on SYNSORB is particularly useful for binding verotoxin.

For the purpose of this application, all sugars are referenced using conventional three letter nomenclature. All sugars are assumed to be in the D-form unless otherwise noted, except for fucose, which is in the L-form. Further, all sugars are in the pyranose form.

For the purposes of this application, the presentation of the infection is determined after the identification of at least one condition associated with an SLT mediated *E. coli* infection. Such conditions include, for example, patients with diarrhea and one of the following: abdominal cramping, blood in the stool, rectal prolapse, detection of a verotoxin-producing *E. coli* in the patient's stool; ingestion of food suspected of containing a verotoxin-producing *E. coli*; or close contact with an individual known to have an SLT mediated infection. Preferably, the presentation of the infection is manifested by bloody diarrhea. In a particularly preferred embodiment, the initial clinical evaluation that the individual is afflicted with an SLT mediated *E. coli* infection is confirmed via diagnostic evaluation of the stool. One diagnostic tool commercially available for detecting SLT mediated *E. coli* infection is sold by Meridian Diagnostic, Inc., Cincinnati, Ohio, USA 45244 under the name Premier EHEC.

B. Synthesis

Synthesis of antibiotics can be accomplished by methods known in the art. Antibiotics useful in the present invention include those antibiotics useful to treat enterohemorrhagic *E. coli* infections, that is to say, antibiotics to which the organism is sensitive, i.e., not resistant. Antibiotics which are bactericidal rather than bacteriostatic are preferred. Antibiotics which do not react with the co-administered oligosaccharide-support compositions should be used. Such antibiotics are known to or may be selected by those of skill in the art. (See e.g., Goodman and Gilman, *The Pharmacological Basis of Therapeutics,* 7th Ed., the disclosure of which is incorporated herein by reference.) Particularly preferred antibiotics include cefixime, ciprofloxacin, co-trimoxazole, mitomycin-C, fosfomycin, kanamycin, azithromycin, tetracycline, minocycline, cefditoren/cefteram, norfloxacin, chloramphenicol, streptomycin, ampicillin, sulfamethoxazole-trimethoprim and nalidixic acid [56,57].

Chemical methods for the synthesis of oligosaccharide structures can be accomplished by methods known in the art.

These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established.

A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [12–28].

The supports to which the oligosaccharide structures of the present invention are bound or immobilized include a wide variety of biocompatible materials known in the art. Water soluble biocompatible polymers such as hydrogels, carboxymethyl celluloses, synthetic polymers, and the like are particularly preferred. In particular, these supports are useful for delivery to the gut, especially prolonged delivery. Useful supports are non-absorbable, that is to say that they may be soluble or insoluble, so long as they are not absorbed by the body.

Solid supports are particularly useful for certain applications. Such solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferably the solid supports have a particle size of from about 10 to 500 microns for in vivo use. In particular, particle sizes of 100 to 200 microns are preferred.

The oligosaccharide structure(s) is covalently bound or noncovalently (passively) adsorbed onto the support so as to be immobilized to form an oligosaccharide-support structure. The covalent bonding may be via reaction between functional groups on the support and the compatible linker arm of the oligosaccharide structure. It has unexpectedly been found that attachment of the oligosaccharide structure to the biocompatible support through a compatible linking arm provides a product which, notwithstanding the support, effectively removes toxin. Linking moieties that are used in indirect bonding are preferably organic bifunctional molecules of appropriate length (at least one carbon atom) which serve simply to distance the oligosaccharide structure from the surface of the support.

The oligosaccharide-support compositions of this invention are preferably represented by the formula:

(OLIGOSACCHARIDE-Y—R)$_n$-SUPPORT where OLIGOSACCHARIDE represents an oligosaccharide group of at least 1 sugar unit which group binds to SLT, Y is oxygen, sulfur or nitrogen, R is an aglycon linking arm of at least 1 carbon atom, SUPPORT is as defined above, and n is an integer greater than or equal to 1. Oligosaccharide sequences containing about 2 to 10 saccharide units may preferably be used. Sequences with about 2 to 6 saccharide units and/or comprising the αGal(1→4)βGal subunit are preferred. In some instances, more than one SLT binding oligosaccharide group may be linked to the support. Preferably, n is such that the composition contains about 0.25 to 2.50 micromoles oligosaccharide per gram of composition.

Numerous aglycon linking arms are known in the art. For example, a linking arm comprising a para-nitrophenyl group (i.e., —OC$_6$H$_4$pNO$_2$) has been disclosed [29]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [30]. Specifically, the linking arm is derived from a 2-bromoethyl group which, in a substitution reaction with thionucleophiles, has been shown to lead to linking arms possessing a variety of terminal functional groups such as, —OCH$_2$CH$_2$SCH$_2$CO$_2$CH$_3$ and —OCH$_2$CH$_2$SC$_6$H$_4$—pNH$_2$. These terminal functional groups permit reaction to complementary functional groups on the support, thereby forming a covalent linkage to the support. Such reactions are well known in the art.

A 6-trifluoroacetamido-hexyl linking arm, (—O—(CH$_2$)$_6$—NHCOCF$_3$) has been disclosed [31] in which the trifluoroacetamido protecting group can be removed, unmasking the primary amino group used for coupling.

Other exemplifications of known linking arms include the 7-methoxycarbonyl-3,6,dioxaheptyl linking arm [32] (—OCH$_2$—CH$_2$)$_2$OCH$_2$CO$_2$CH$_3$); the 2-(4-methoxycarbonyl-butancarboxamido)ethyl [33] (—OCH$_2$CH$_2$NHC(O)(CH$_2$)$_4$CO$_2$CH$_3$); the allyl linking arm [34] (—OCH$_2$CH=CH$_2$) which, by radical co-polymerization with an appropriate monomer, leads to co-polymers; other allyl linking arms [35] are known [—O(CH$_2$CH$_2$O)$_2$CH$_2$CH=CH$_2$]. Additionally, allyl linking arms can be derivatized in the presence of 2-aminoethanethiol [36] to provide for a linking arm —OCH$_2$CH$_2$CH$_2$SCH$_2$CH$_2$NH$_2$. Other suitable linking arms have also been disclosed [12–14,16,17]. The particular linking employed to covalently attach the oligosaccharide group to the support is not critical.

Preferably, the aglycon linking arm is a hydrophobic group and most preferably, the aglycon linking arm is a hydrophobic group selected from the group consisting of

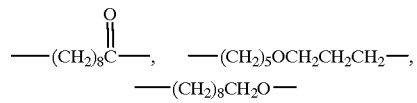

and —NH—(CH$_2$)$_m$—NHC(O)NH—, where m is an integer of from about 2 to about 10.

In studies using rats (a widely accepted model for preclinical studies, since they are predictive of human response), SYNSORBs have been found to pass unaffected through the rat gastrointestinal tract. They were found to be eliminated completely and rapidly (99% eliminated in 72 hours) following oral administration. Additionally, the high density of oligosaccharide moieties on SYNSORBs is particularly useful for binding toxins which have carbohydrate binding affinity.

Non-peptidyl linking arms are preferred for use as the compatible linking arms of the present invention. The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable due to questionable stability in the gastrointestinal tract when given orally.

Covalent attachment of an oligosaccharide group containing an SLT binding unit through a non-peptidyl spacer arm to an inert support permits efficient binding and removal of toxin from the intestine of a patient suffering from or susceptible to a condition associated with enterohemorrhagic *E. coli* infection. When the oligosaccharide is synthesized with this compatible linker arm attached (in non-derivatized form), highly pure compositions may be achieved which can be coupled to various supports.

The oligosaccharide is coupled to a support or coupled directly, preferably through a linking arm such as that described by Lemieux, et al. [11]. The di and trisaccharide units may also be coupled directly to pharmaceutically acceptable carriers or constitute a portion of an oligosaccharide coupled to such carriers.

The inert affinity supports comprising an αGal(1→4)βGal subunit which is bound to said support through a non-peptidyl linker arm preferably used in the methods of this invention are made by methods known in the art [11,12,61] as follows. In each case the 8-methoxycarbonyloctyl glycoside of the respective hapten is activated and ligated to a silylaminated solid support, wherein the matrix is comprised of $SiO_2$, followed by the acetylation of the remaining amine groups on the solid support. These formulations are:

$P_1$-di, which contains at least 0.25 μmol/g αGal(1-4)βGal disaccharide;

$P_1$-tri, which contains at least 0.25 μmol/g αGal(1-4)βGal (1-4)βGlcNAc trisaccharide; and $P_k$-tri, which contains at least 0.25 μmol/g αGal(1-4)βGal (1-4)βGlc trisaccharide.

C. Pharmaceutical Compositions

The methods of this invention are achieved by simultaneously administering a composition which binds SLT whenever an antibiotic is administered to a subject suffering from or susceptible to pathogenic *E. coli* infection. The antibiotic may be formulated and administered in any useful form and by any useful route of administration known to those of skill in the art. Preferably, pharmaceutical compositions comprising an amount of at least one antibiotic effective to treat an *E. coli* infection and an amount of one or more oligosaccharide structures which bind SLT and/or verotoxin attached to a support effective to bind SLT and/or verotoxin present in the gut of the subject are used.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art. (See, e.g., *Remington's Pharm. Sci.,* 18th Ed., 1990.)

Compositions which may be mixed with liquid or semi-solid foods such as enteral nutritional formulas, applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The (OLIGOSACCHARIDE-Y—R)$_n$-SUPPORT composition itself may also be used without the addition of inert pharmaceutical carriers, particularly for use in capsule form. When a pharmaceutically inert carrier is employed the carrier is typically employed in the amount ranging from about 1 to about 99 percent based on the total weight of the composition and more preferably from about 75 to about 95 weight percent.

The dose of antibiotics used depends on such factors as the particular antibiotic, the condition of the subject, the route of administration. Doses are selected to effectively kill the pathogenic *E. coli* in an infected subject. Selection of appropriate doses is well known to those of skill in the art.

Doses of oligosaccharide-support are selected to provide neutralization and elimination of SLT found in the gut of effected subjects. Preferred useful doses are from about 0.25 to 1.25 micromoles of oligosaccharide/kg body weight/day, most preferably about 0.5 to 1.0 micromoles of oligosaccharide/kg body weight/day. Using SYNSORB compositions, this means about 0.5 to 1.0 gram SYNSORB/kg body weight/day, which gives a concentration of SYNSORB in the gut of about 20 mg/ml. Administration is expected to be 2 to 4 times daily, for a period of one week or until clinical symptoms are resolved. The dose level and schedule of administration may vary depending on the particular antibiotic and/or oligosaccharide structure used and such factors as the age and condition of the subject and the extent of the disease condition, all of which are well within the skill of the art.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain an effective amount of antibiotic, i.e., an amount of antibiotic effective to treat the *E. coli* infection, and about 1 micromole oligosaccharide/ml.

D. Methodology

SLT toxin may be neutralized by oligosaccharide sequences comprising the αGal(1→4)βGal subunits which sequences bind the toxin. In particular, such oligosaccharide sequences covalently attached to supports have been found to neutralize SLT toxin effectively. Examples of such compositions are certain SYNSORBs, which bind and neutralize SLT toxin activity.

The antibiotics useful in the present invention are those which effectively treat an *E. coli* infection when administered to an infected subject. Bactericidal antibiotics are preferred. They may be administered orally, parenterally (e.g., intravenously, intramuscularly, subcutaneously, etc.) or by other routes. Administration of SLT binding oligosaccharide-support compositions alone prior to antibiotic administration may be used to initially clear SLT from the subject. When an antibiotic is used which requires a different schedule of dosing than the SLT binding oligosaccharide-support composition, e.g., when the antibiotic is only administered once a day, additional administration of SLT binding oligosaccharide-support compositions alone may be used to provide continued clearing of SLT throughout the day. The key to the claimed invention is that each time an antibiotic is administered, an SLT binding oligosaccharide-support composition is also administered to the subject. Preferably, the antibiotic is administered in pharmaceutical admixture with an oligosaccharide-support which binds SLT.

The oligosaccharide sequences attached to supports useful in the present invention include those which bind SLT toxin. The binding affinity of an oligosaccharide to SLT toxin is readily detectable by a simple in vitro tests. For the purposes of this invention, oligosaccharide sequences attached to supports which bind SLT toxin means those compositions which reduce endpoint titers from cytotoxic activity in Vero cell assays by at least 50% and preferably by at least 95%, using an assay known to those in the art.

Other oligosaccharide sequences attached to supports useful in the present invention are those which can bind SLT toxin significantly better ($p \leq 0.05$, using appropriate standard statistical methods, such as the Wilcoxon or Student's T-test) than a control support that does not contain any attached oligosaccharide sequences (e.g., CHROMOSORB P).

The effect of the compositions of the invention in neutralizing SLT can be measured by comparing activity of the SLT with and without treatment with the compositions. Activity of the SLT can be assayed by taking advantage of the toxicity of these compounds to Vero cells. Vero cells (ATCC CCL81) can be obtained from the American Type Culture Collection, Rockville, Md.

In the methods of this invention, the clinical incidence of HUS arising from enterohemorrhagic E. coli infection is reduced when the pharmaceutical compositions described above are administered within 3 days of presentation of the infection and prior to organ involvement other than intestinal involvement. Contrarily, administration of this pharmaceutical composition after this time frame when organs other than the intestine are involved in the infection substantially reduces the ability of this composition to reduce the incidence of HUS.

Preferably, the initial clinical evaluation that the individual is afflicted with an SLT mediated E. coli infection is confirmed via diagnostic evaluation of the stool. One diagnostic tool commercially available for detecting SLT mediated E. coli infection is sold by Meridian Diagnostic, Inc., Cincinnati, Ohio, USA 45244 under the name Premier EHEC.

As can be appreciated from the disclosure above, the present invention has a wide variety of applications. Accordingly, the following examples are offered by way of illustration and not by way of limitation.

EXAMPLE 1

Evaluation of SYNSORB-$P_k$ Neutralization of Verotoxin Activity Expressed by E. coli O157:H7 Exposed to Antibiotics A. Determination of E. coli O157:H7 MIC's.

The minimum inhibitory concentrations (MIC's) of various antibiotics for E. coli O157:H7 (EEU 396, which produces both VT 1 and VT 2) were determined according to the procedure described in the Antimicrobial Susceptibility Testing Manual, $3^{rd}$ Ed. (NCCLS Document M7-A2, Vol. 10, No. 8), using E. coli American Type Culture Collection (ATCC) strain 25922 to validate the procedure.

The MIC's for the various antibiotics tested are listed in Table 1.

TABLE 1

Minimum Inhibitory Concentrations of Antibiotics for E. coli O157:H7 and Reference Strain ATCC 25922

| E. coli Strain | Antibiotic ($\mu$g/ml) | | | | |
|---|---|---|---|---|---|
| | Cefixime | Tetracycline | Ciprofloxacin | Co-trimoxazole (trimethoprim/ sulfamethox-asole) | Mitomycin-C |
| O157:H7 (EEU396) | 4.8 | 1.92 | 0.192 | 0.96/4.8 | 9.6 |
| ATCC #25922 | 0.96 | 1.92 | 0.0384 | 0.96/4.8 | 9.6 |

B. Growth and Treatment of E. coli O157:H7 With Antibiotics and SYNSORB-$P_k$

E. coli O157:H7 bacteria were grown overnight in Mueller-Hinton (MH) broth, 200 mL in a 1 L Erlenmeyer flask, at 37° C. on a New Brunswick Gyrotory shaker table, Model No. G10, at 120 rpm. This overnight culture was then diluted to an O.D. of 0.6 at 625λ and 50 mL aliquots were proportioned into 125 mL Erlenmeyer flasks.

Antibiotics were added at concentrations based on the MIC's determined above, essentially as recommended by Walterspiel, J. N., et al. (Infection, 1992, 20:25–9) [62] and the cultures were incubated for an additional 24 h with shaking at 37° C. The final concentrations of each of the antibiotics in the 24 h cultures were half the MIC's to maximize verotoxin production by the E. coli O157:H7. Duplicate flasks were prepared for each of the antibiotics tested. SYNSORB-$P_k$, at a concentration of 10 mg/mL, was added to one of each of the pairs of flasks at the same time as the antibiotics.

The amount of verotoxin in each of the 24 h cultures was then determined using the verocytotoxicity assay as described by Armstrong, G. D., et al. (J. Infect. Dis., 1991, 164:1160–7) [53]. The results were plotted and the $CD_{50}$ values for the SYNSORB-$P_k$-treated and untreated antibiotic cultures were extrapolated from the resulting graphs. The percent neutralization of verotoxin activity in the SYNSORB-$P_k$-treated antibiotic cultures relative to the untreated antibiotic cultures was calculated using the formula in Armstrong, G. D., et al., 1991 [53].

The percent neutralization of verotoxin activity by SYNSORB-$P_k$ in *E. coli* O157:H7 cultures exposed to various antibiotics is presented in Table 2.

TABLE 2

SYNSORB-$P_k$ Neutralization of Verotoxin Activity in the Presence of Antibiotics

| Antibiotic ($\mu$g/ml) | SYNSORB-$P_k$ (10 mg/ml) | $CD_{50}$[b] | Percent Neutralization |
|---|---|---|---|
| Tetracycline | + | 0.0 | 100 |
| (0.96) | – | 15.8 | |
| Ciprofloxacin | + | 5.0 | 90 |
| (2.4) | – | 50.1 | |
| Co- | + | 0.0 | 100 |
| Trimoxazole | – | 63.1 | |
| (0.48) | | | |
| Cefixime | + | 0.0 | 100 |
| (2.4) | – | 316.2 | |
| Mitomycin-C | + | 0.0 | 100 |
| (0.96) | – | 158.4 | |

[b]Number of dilutions required to reach $CD_{50}$

These data show that a treatment protocol using a combination of antibiotics and SYNSORB-$P_k$ may be effective in reducing serious complications, such a HUS, in patients suffering from an *E. coli* O157:H7 infection. As demonstrated by these neutralization data, SYNSORB-$P_k$ binds to verotoxins expressed by *E. coli* O157:H7 in the presence of antibiotics.

Similarly, it will bind to verotoxins released by dying, antibiotic-treated bacteria and prevent their absorption into the circulatory system. This will allow the antibiotics to eliminate the organisms without increasing the chances of HUS developing in these patients.

EXAMPLE 2

Treatment of *E. coli* Infection

Within 3 days of presentation of infection with an enterohemorrhagic *E. coli* such as O157:H7, patients will be treated two times per day with a composition comprising an effective amount of a suitable antibiotic such as kanamycin and 250 mg/kg SYNSORB-$P_k$ mixed in baby food. Measurement of SLT present in the gut content will show reduced SLT levels and treated patients will not develop HUS as compared to untreated patients, patients receiving only antibiotic, patients receiving only SYNSORB-$P_k$ or patients receiving antibiotic and SYNSORB-$P_k$ at different times of administration rather than simultaneously.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

The disclosure of each publication, patent or patent application mentioned in this specification is hereby incorporated by reference to the same extent as if each individual publication, patent or patent application were specifically and individually indicated to be incorporated by reference.

What is claimed is:

1. A method to prevent or ameliorate one or more conditions mediated by enterohemorrhagic *E. coli* in a patient suffering from or susceptible to said condition, comprising the steps of:

a) administering to the patient an amount of at least one shiga-like toxin (SLT) binding oligosaccharide sequence covalently attached to a pharmaceutically acceptable inert support (oligosaccharide-support), wherein said oligosaccharide sequence blinds SLT and said amount is effective to provide neutralization and elimination of the SLT present in the gut of the patient wherein said oligosaccharide-support is an 8-methoxycarbonyloctyl oligosaccharide covalently coupled to derivatized silica particles; and, after step a)

b) simultaneously administering to the patient an amount of at least one antibiotic, said amount of said antibiotic being effective to kill the pathogenic *E. coli* in the patient and an amount of at least one SLT binding oligosaccharide sequence covalently attached to a pharmaceutically acceptable inert support (oligosaccharide-support), wherein said oligosaccharide sequence binds SLT and said amount is effective to provide neutralization and elimination of the SLT present in the gut of the patient wherein said oligosaccharide-support is an 8-methoxycarbonyloctyl oligosaccharide covalently coupled to derivatized silica particles, and wherein, following each administration, the SLT bound to said oligosaccharide-support is capable of being eliminated from the gastrointestinal tract.

2. The method of claim 1 wherein the antibiotic is cefixime, tetracycline, ciprofloxacin, co-trimoxazole, mitomycin-C, fosfomycin and kanamycin.

3. The method of claim 1 wherein the oligosaccharide comprises the $\alpha$Gal(1→4)$\beta$Gal subunit.

4. The method of claim 1 wherein the oligosaccharide is selected from the group consisting of $\alpha$Gal(1→4)$\beta$Gal, $\alpha$Gal(1→4)$\beta$Gal(1→4)$\beta$GlcNAc and $\alpha$Gal(1→4)$\beta$Gal(1→4)$\beta$Glc.

5. The method of claim 1 wherein the oligosaccharide is bound to the support using a non-peptidyl linker.

6. The method of claim 1 wherein a single pharmaceutical composition containing the antibiotic and the SLT binding oligosaccharide-support is administered following the initial administration of toxin binding composition alone.

7. The method of claim 1 wherein the administration is performed within about 3 days of presentation of the infection.

8. The method of claim 1 wherein said oligosaccharide sequence has from 2 to 10 saccharide units.

9. The method of claim 1 wherein the administration to the patient is performed prior to organ involvement other than intestinal involvement.

* * * * *